(12) United States Patent
St. George-Hyslop et al.

(10) Patent No.: US 7,371,920 B2
(45) Date of Patent: May 13, 2008

(54) TRANSGENIC MOUSE MODEL OF NEURODEGENERATIVE DISORDERS

(75) Inventors: Peter H. St. George-Hyslop, Toronto (CA); Paul E. Fraser, Toronto (CA); David Westaway, Etobicoke (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 25 days.

(21) Appl. No.: 09/884,629

(22) Filed: Jun. 19, 2001

(65) Prior Publication Data

US 2003/0093822 A1 May 15, 2003

Related U.S. Application Data

(60) Provisional application No. 60/212,534, filed on Jun. 20, 2000.

(51) Int. Cl.
*A01K 67/00* (2006.01)
*A01K 67/033* (2006.01)
*A01K 67/027* (2006.01)
*C12N 15/00* (2006.01)

(52) U.S. Cl. ............... 800/18; 800/21; 800/8; 800/12; 800/13; 800/14

(58) Field of Classification Search ............ 800/3, 800/8, 12, 13, 18, 25, 21, 9, 14
See application file for complete search history.

(56) References Cited

U.S. PATENT DOCUMENTS

| | | | | |
|---|---|---|---|---|
| 5,455,169 A | * | 10/1995 | Mullan | 435/325 |
| 5,612,486 A | | 3/1997 | McConlogue et al. | 800/2 |
| 5,672,805 A | * | 9/1997 | Neve | 800/3 |
| 5,850,003 A | | 12/1998 | McLonlogue et al. | 800/2 |
| 5,877,399 A | | 3/1999 | Hsiao et al. | 800/2 |
| 5,894,078 A | | 4/1999 | Nalbantoglu et al. | 800/2 |
| 5,898,094 A | | 4/1999 | Duff et al. | 800/2 |
| 6,037,521 A | * | 3/2000 | Sato et al. | 800/18 |
| 6,117,978 A | | 9/2000 | St. George-Hyslop et al. | 530/350 |
| 6,175,057 B1 | * | 1/2001 | Mucke et al. | 800/12 |
| 6,262,335 B1 | * | 7/2001 | Hsiao et al. | 800/12 |
| 6,509,515 B2 | * | 1/2003 | Hsiao et al. | 800/12 |
| 2001/0016951 A1 | * | 8/2001 | Sommer et al. | 800/3 |

FOREIGN PATENT DOCUMENTS

| | | |
|---|---|---|
| WO | WO 96/34099 | 10/1996 |
| WO | WO 96/40895 | 12/1996 |
| WO | WO 99/09150 | 2/1999 |

OTHER PUBLICATIONS

Lannfelt et al. Behav Brain Res (1993), 57:207-213.*
Felsenstein et al. Alz Parkinson's Diseases (1995) Hannin et al (Eds.), Plenum Pres, New York, NY, pp. 401-409.*
Higgins et al.Annals NY Acad Sci (1993) 695:224-227.*
Hammer et al. 1986, J. of Anim. Sci., 63: 269-278.*
Andra et al., 1996, Neurobiology of Aging, 17: 183-190.*
Carlson et al., 1997, Human Molecular Genetics, 6: 1951-1959.*
Hisao et al., 1995, Neuron, 15: 1203-1218.*
Chishti, et al., 2001, Journal of Biological Chemistry, 276: 21562-21570.*
Hsia et al., 1999, PNAS, USA, 96: 3228-3233.*
Jin et al., 2004, PNAS, USA, 101, 13363-13367.*
Selkoe, 2002, Science, 298, 789-791.*
Blast [online], 2006 [retrieved on Dec. 7, 2006]. Retrieved from the Internet:< URL: <http://www.ncbi.nlm.nih.gov/BLAST/Blast/cgi>, 2 pages.*
Van Leuven, F. (2000) "Single and multiple transgenic mice as models for Alzheimer's Disease", Prog. Neurobiol., 61: 305-312.
Sturchler-Pierrat, C. et al., (1997) "Two amyloid precursor protein transgenic mouse models with Alzheimer disease-like pathology", Proc Natl Acad Sci USA 94(24), 13287-92.
Hsia Ay et all, (1999) "Plaque-independent disruption of neural circuits in Alzheimer's disease mouse models", Proc Natl Acad Sci USA. 96,3228-33.
McGowan et al., (1999) "Amyloid Phenotype Characterization of Transgenic Mice Overexpressing both Mutant Amyloid Precursor Protein and Mutant Presenilin 1 Transgenes", Neurobiol. of Disease, 6:231-244.
Holcomb L., Gordon MN., McGowan E., et al. (1998) Accelerated Alzheimer-type phenotype in transgenic mice carrying both mutant *amyloid precursor protein* and *presenilin 1* transgenes, Nature Med., 4:97-100.
Kang, J. et al., (1987) "The precursor of Alzheimer disease amyloid A4 protein resembles a cell-surface receptor", Nature, 325:733-736.
Mullan, M.J., et al., (1992) "A pathogenic mutation for probable Alzheimer's Disease in the APP gene at the N-terminus of B-amyloid", Nature Genetics, 1:345-347.
Murrell, J., et al., (1991) "A mutation in the amyloid precursor protein associated with hereditary Alzheimer's Disease", Science, 254:97-99.
Citron M., et al., (1992) "Mutation of the B-amyloid precursor protein in familial Alzheimer's Disease increases B-protein production", Nature, 360:672-674.
Citron, M., et al., (1994) "Excessive production of amyloid B-Protein by peripheral cells of symptomatic and presypmtomatic patients carrying the Swedish Familial Alzheimer's Disease mutation", Proc. Natl. Acad. Sci. USA, 91:11993-11997.
Haass, C., et al., (1995) "The Swedish mutation causes early onset Alzheimer's disease by B-secretase cleavage within the secretory pathway", Nature Med., 1:1291-1296.

(Continued)

*Primary Examiner*—Anne Marie Wehbe
*Assistant Examiner*—Joanne Hama
(74) *Attorney, Agent, or Firm*—Ropes & Gray, LLP; James F. Haley, Jr.; Raymond M. Doss

(57) ABSTRACT

The present invention provides a transgenic animal model of Alzheimer's Disease designated TgCRND8 as well as a method for making such model, which allows for the characterization of the etiology of the disease as well as for provide a system for the development and testing of potential treatments.

7 Claims, No Drawings

OTHER PUBLICATIONS

Haass, C., et al., (1991) "Processing of Beta-Amyloid precursor protein in microglia and astrocytes favours an internal localization over constitutive secretion", J. Neurosci., 11:3783-3793.

Haass; C., et al., (1994) Mutations associated with locus for familial Alzheimer's Disease result in alternative processing of amyloid B-protein precursor, J. Biol. Chem., 269:17741-17748.

Shoji, M., et al., (1992) "Production of the Alzheimer amyloid B protein by normal proteolytic processing", Science, 258: 126-129.

Scott, M.R., et al., (1992) "Chimeric prion protein expression in cultured cells and transgenic mice", Protein Sci., 1:986-997.

Nee, L., et al., (1983) "A family with histologically confirmed Alzheimer Disease", Arc. Neurol., 40:203-208.

Foncin, J.-F., et al., (1985) "Alzheimer's Presenile dementia transmitted in an extended kindred", Rev. Neurol. (Paris), 141:194-202.

Frommelt., P., et al., (1991) "Familial Alzheimer Disease: A Large Multigenerational German Kindred", Alzheimer Dis. Assoc. Disorders, 5:406-412.

Lippa, C.F., et al., (1996) "Familial and sporadic Alzheimer's disease: neuropathology cannot exclude a final common pathway", Neurology, 46:406-412.

Lippa, C.F., et al., (1998) "Abeta42 deposition precedes other changes in PS1 Alzheimer's Disease", Lancet, 352:1117-1118.

Games, D., et al., (1995) "Alzheimer-type neuropathology in transgenic mice overexpressing V717F beta-amyloid precursor protein", Nature, 373:523-527.

Hsiao, K., et al., (1996) "Correlative memory deficits, Abeta elevation, and amyloid plaques in transgenic mice", Science, 274:99-102.

Moechars, D.,et al., (1999) "Early phenotypic changes in transgenic mice that overexpress different mutants of amyloid precursor protein", J. Biol. Chem., 274:6483-6492.

Citron, M., et al., (1998) "Additive effects of PS1 and APP mutations on secretion of the 42-residue amyloid beta-protein", Neurobiol. Dis., 5:107-116.

Borchelt, D.R., et al., (1998) "Accelerated amyloid deposition in brains of transgenic mice coexpressing mutant presenilin 1 and amyloid precursor proteins", Neuron, 19:939-945.

Palmiter, R.D., and Brinster, R.L., (1986) "Germ-line transformation of mice", Annu. Rev. Genet. 20:465-499.

Lu et al., (2000) "A second cytotoxic proteolytic peptide derived from amyloid beta-protein precursor", Nature Medicine, 6:397-404.

Schenk, D., et al., (1999) "Immunization with amyloid-beta attenuates Alzheimer-Disease-like pathology in the PDAPP mouse", Nature, 400:173-177.

Carlson, G.A., et al., (1997) Genetic modification of the phenotypes produced by amyloid precursor protein overexpression in transgenic mice, Hum. Mol. Genet., 6:1951-1959.

Scott et al., (1989) "Transgenic mice expressing hamster prion produce species-specific scrapie infectivity and amyloid plaques", Cell 59:847-857.

Morris, R.G.M., (1984) "Developments of a water-maze procedure for studying spatial learning in the rat", J. Neuroscience Methods, 11:47-60.

Janus, C., D'Amelio, S., Amitay, O., Chishti, M.A., Strome, R., Fraser, P.E., Carlson, G.A., Roder, J., St. George-Hyslop, P. and Westway, D., (2000) "Spatial learning in transgenic mice expressing human presenilin 1 (PS1) transgenes", Neurobiology Aging, 21:541-549.

Feinberg, A.P., and Vogelstein, B., (1983) "A technique for radiolabeling DNA restriction endonuclease fragments to high specific activity", Anal. Biochem., 132:6-13.

Citron, M., et al. (1997) "Mutant presenilins of Alzheimer's disease increase production of 42-residue amyloid beta-protein in both transfected cells and transgenic mice", Nature Medicine, 3:67-72.

Forss-Petter et al., (1990) "Transgenic mice expressing beta-galactosidase in mature neurons under neuron-specific enolase promoter control", Neuron 5:187-97.

Sasahara et al., (1991) "PDGF B-chain in neurons of the central nervous system, posterior pituitary, and in a transgenic model", Cell 64:217-227.

Prusiner et al., (1990) "Transgenic studies implicate interactions between homologous PrP isoforms in scarpie prion replication", Cell 63:673-686.

Andra, K., et al., (1996) "Expression of APP in transgenic mice: a comparison of neuron-specific promoters", Neurobiol. Aging, 17:183-190.

Skovronsky, D. M. et al.: "Beta-Secretase revealed: starting gate for race to novel therapies for Alzheimer's disease"Trends in Pharmacological Sciences, Elsevier Trends Journal, Cambridge, GB, vol. 21, No. 5, May 2000, pp. 161-163, XP004198178.

Hussain, M. M. et al.: "The Mammalian Low-Density Lipoprotein Receptor Family," Annual Review of Nutrition, Annual Reviews Inc., Palo Alto, CA, US, vol. 19. 1999, pp. 141-172, XP001024478.

Van Uden, E. et al.: "Aberrant Presenilin-1 Exoression Downregulates LDL Receptor-Related Protein (LRP): Is LRP Central to Alzheimer's Disease Pathogenesis," Molecular and Cellular Neurosciences, San Diego, US, vol. 2, No. 14, Aug. 1999, pp. 129-140, XP001074728.

Tomita, T. et al.: "Molecular Dissection of Domains in Mutant Presenilin 2 That Mediate Overproduction of Amyloidogenic Forms of Amyloid Beta Peptides, Inability of Truncated Forms of PS2 With Familial Alzheimer's Disease Mutation to Increase Secretion of A-beta-42," Journal of Biological Chemistry, American Society of Biological Chemists, Baltimore, MD, US, vol. 273, No. 33, Aug. 14, 1998, XP002928398.

Chui, D-H. et al.: "Transgenic mice with Alzheimer preseniin 1 mutations show accelerated neurodegeneration without amyloid plaque formation," Nature Medicine, Nature Publishing, CO, US, vol. 5, No. 5, May 1999, pp. 560-564, XP001015693.

Wong, T.P. et al.: "Reorganization of Cholinergic Terminals in the Cerebal Cortex and Hippocampus in Transgenic Mice Carrying Mutated Presenilin-1 and Amyloid Precusor Protein Transgenes," Journal of Neuroscience, New York, NY, US, vol. 19, No. 7, Apr. 1, 1999, pp. 2706-2716, XP000978979.

Holcomb, L.A. et al.: "Behavioral Changes in Transgenic Mice Expressing Both Amyloid Precursor Protein and Presenilin-1 Mutations: Lack of Association with Amyloid Deposits," Behavior Genetics, New York, NY, US, vol. 29, No. 3, May 1999 pp. 177-185, XP000978983.

Gervais et al., "Targeting Soluble Aβ Peptide With Tramiprosate for the Treatment of Brain Amyloidosis", Neurobiology of Aging, 28:537-547 (2007).

* cited by examiner

TRANSGENIC MOUSE MODEL OF NEURODEGENERATIVE DISORDERS

This application claims priority from U.S. Provisional Application No. 60/212,534, which was filed in the United States Patent and Trademark Office on Jun. 20, 2000.

FIELD OF THE INVENTION

The present invention relates to transgenic non-human animal models of neurodegenerative disorders, including Alzheimer's Disease. More specifically, the present invention is directed to a murine model which facilitates the characterization of the pathogenic mechanisms of Alzheimer's disease and the development of diagnostics, therapies and therapeutic compounds.

BACKGROUND OF THE INVENTION

In the description which follows, references are made to certain literature citations which are listed at the end of the specification and all of which are incorporated herein by reference.

Alzheimer's Disease (AD), the most common cause of dementia, has a complex etiology that most likely involves genetic and environmental determinants. It is characterized by cerebral amyloid deposits formed from the amyloid beta-peptide (Aβ), neuronal loss, and intracellular deposits known as neurofibrillary tangles (NFTs), composed of hyper-phosphorylated forms of the microtubule-associated protein tau (τ).

Genetic analysis of diverse familial Alzheimer's Disease (FAD) kindreds indicates that biosynthesis of the amyloid beta-peptide (Aβ) is a common denominator in the disease pathogenesis. In the case of chromosome 21-linked kindreds, mutations flank the endoprotease sites where Aβ is excised from the Alzheimer amyloid precursor protein (APP), whereas mutations in presenilins 1 and 2 are thought to enhance cleavage of APP at the C-terminal boundary of Aβ, the so-called γ-secretase site. Though the tau gene on chromosome 17 is not mutated in AD, missense substitutions and splice site mutations are present in conditions with some pathological similarities to AD, such as fronto-temporal dementia.

The genetic data indicate that Aβ biogenesis lies upstream in a pathogenic pathway that culminates in the generation of NFTs. While earlier debates focussed upon whether Aβ amyloid or NFTs cause neuronal loss and dysfunction, it now seems likely that both types of protein aggregate are toxic and contribute to the clinical phenotype of AD.

Although there are no naturally occurring animal forms of AD, transgenic animal models of the disease have the potential to clarify and order the key pathogenic events in the human disease. Despite intense effort, however, few satisfactory models exist.

U.S. Pat. No. 5,877,399 relates to transgenic mice expressing human or mouse $APP_{695}$, either wild type or bearing the "Swedish" mutation, and developing a progressive neurologic disorder generally within a year from birth. U.S. Pat. No. 6,037,521 relates to an animal model of Alzheimer's Disease having a transgene which encodes a 99 to 103 amino acid carboxy-terminus portion of human APP. U.S. Pat. No. 5,894,078 relates to a transgenic mouse whose genome comprises a DNA sequence encoding the carboxy-terminal 100 amino acids of human βAPP inserted into exon I of the neurofilament gene. U.S. Pat. No. 5,850,003 relates to transgenic mice harboring a transgene encoding human $APP_{751}$ with the Swedish mutation.

U.S. Pat. No. 5,898,094 relates to a transgenic animal model of AD wherein the animal bears and expresses both a mutant presenilin 1 transgene and an $APP_{695}$ transgene carrying the Swedish mutation.

Some of these models fail to produce APP and/or its metabolites by physiologically appropriate pathways, and in cases where this caveat does not apply, the transgenic animals may display only certain facets of the AD phenotype. With respect to neuropathology, there may be amyloid deposits that very closely resemble those seen in AD, selective neuronal loss (in one instance) and hyperphosphorylation of tau, but no deposition of NFTs. Additionally, these neuropathological abnormalities may not appear until 8-9 months of age, or until 6 months of age in the case of bigenic or homozygous animals. Other complications encountered in the creation of these models include neonatal lethality attributed to overexpression of APP, the use of complex genetic backgrounds, and generally no clear evidence of progressive cognitive dysfunction.

There is therefore a need for a transgenic animal model of AD that rapidly displays the important facets of the human AD phenotype, so that animals need not be maintained for extended periods of time and diagnostics and therapeutic compounds can be developed and screened much more rapidly and cost effectively.

SUMMARY OF THE INVENTION

The present invention relates to a new animal model of AD comprising a transgenic mammal, comprising in a preferred embodiment a transgenic mouse designated TgCRND8, that exhibits high levels of Aβ synthesis and amyloid deposition in the CNS by 3 months of age. Furthermore, TgCRND8 mice exhibit cognitive changes within the time period in which amyloid deposition commences. The present invention also provides methods for the production of the TgCRND8 transgenic animal model of Alzheimer's Disease.

With the development of the TgCRND8 transgenic mouse model for Alzheimer's Disease, the etiology of the disease can be better understood, and potential treatments, including effective drug therapies, can be developed and tested.

The transgenic TgCRND8 mouse model is characterized by a great similarity to the naturally occurring Alzheimer's Disease phenotype, based on the expression of Aβ amyloid protein in the CNS, as well as on histological analysis, neurology and behavioural deficits.

The APP gene undergoes alternative splicing to generate three common isoforms. The longest isoform, containing 770 amino acids ($APP_{770}$), and the second longest isoform containing 751 amino acids ($APP_{751}$), are expressed in most tissues. The third transcript, which contains 695 amino acids ($APP_{695}$), is predominantly expressed in the brain. By convention, the codon numbering of the longest isoform, $APP_{770}$, is used even when referring to codon positions of the shorter isoforms.

The TgCRND8 transgenic mouse contains a transgene expressing a mutant form of the brain-specific $APP_{695}$ isoform; this transgene carries both the "Swedish" and "Indiana" APP mutations.

An $APP_{695}$ cDNA was generated containing (using the codon numbering of $APP_{695}$) the mutations K595N/M596L (the Swedish mutation) and V642F (the Indiana mutation). These and other APP mutations will generally be referred to herein, including the claims, by the more common $APP_{770}$ codon numbering system i.e. for lo these two mutations, K670N/M671L (the Swedish mutation) and V717F (the Indiana mutation).

The double mutant $APP_{695}$ cDNA cassette was inserted into the cosmid expression vector, cosTet, which contains the Syrian hamster prion protein gene promotor. The vector was then microinjected into a mouse oocyte to create a transgenic line designated TgCRND8. These mice exhibit multiple diffuse amyloid deposits by three months of age, at which time deficits in spatial learning are apparent.

In accordance with a further aspect of the invention, TgCRND8 mice have been crossed with various other transgenic mice bearing an AD-related mutation to produce bi-transgenic mice which show further enhanced AD-related neuropathology.

In accordance with one embodiment, the invention provides a transgenic non-human mammal whose genome comprises a transgene comprising a nucleotide sequence operably linked to a promoter and encoding a heterologous amyloid precursor protein 695 ($APP_{695}$) polypeptide wherein the lysine residue at position 670 is substituted by asparagine, the methionine residue at position 671 is substituted by leucine and the valine residue at position 717 is substituted by phenylalanine and wherein the transgene is expressed.

In accordance with a preferred embodiment the mammal is a mouse and the heterologous $APP_{695}$ is human $APP_{695}$.

In accordance with a further embodiment is provided a transgenic non-human mammal produced by:
(a) crossing a first transgenic non-human mammal whose genome comprises a transgene comprising a nucleotide sequence operably linked to a promoter and encoding a heterologous amyloid precursor protein 695 ($APP_{695}$) polypeptide wherein the lysine residue at position 670 is substituted by asparagine, the methionine residue at position 671 is substituted by leucine and the valine residue at position 717 is substituted by phenylalanine and wherein the transgene is expressed with a second non-human mammal having a genome comprising a second gene comprising a nucleotide sequence operably linked to a promoter and encoding a selected protein having at least one selected mutation to produce first generation offspring; and
(b) selecting from the first generation offspring a transgenic non-human mammal having a genome comprising at least one first transgene comprising a nucleotide sequence operably linked to a promoter and encoding a heterologous $APP_{695}$ polypeptide wherein the lysine residue at position 670 is substituted by asparagine, the methionine residue at position 671 is substituted by leucine and the valine residue at position 717 is substituted by phenylalanine and at least one second gene comprising a nucleotide sequence operably linked to a promoter and encoding the selected protein having at least one selected mutation and expressing both the at least one first transgene and the at least one second gene.

In accordance with a further embodiment, the invention provides a transgenic mouse produced by:
(a) crossing a first transgenic mouse whose genome comprises a transgene comprising a nucleotide sequence operably linked to a promoter and encoding a human $APP_{695}$ polypeptide wherein the lysine residue at position 670 is substituted by asparagine, the methionine residue at position 671 is substituted by leucine and the valine residue at position 717 is substituted by phenylalanine and wherein the transgene is expressed, with a second mouse having a genome comprising a second gene comprising a nucleotide sequence operably linked to a promoter and encoding a selected protein having at least one selected mutation to produce first generation offspring; and
(b) selecting from the first generation offspring a transgenic mouse having a genome comprising at least one first transgene comprising a nucleotide sequence operably linked to a promoter and encoding a heterologous $APP_{695}$ polypeptide wherein the lysine residue at position 670 is substituted by asparagine, the methionine residue at position 671 is substituted by leucine and the valine residue at position 717 is substituted by phenylalanine and at least one second gene comprising a nucleotide sequence operably linked to a promoter and encoding the selected protein having at least one selected mutation and expressing both the at least one first transgene and the at least one second gene.

In accordance with a further embodiment, a method is provided for screening a candidate compound for its efficacy in preventing or delaying the development of AD, the method comprising the steps of:
(a) administering the candidate compound to a first transgenic mouse as described herein prior to the appearance of a selected AD-related phenotypic trait in said mouse; and
(b) comparing the age at which said selected AD-related phenotypic trait appears in said mouse with the age at which said trait appears in a second transgenic mouse of the same type to which the compound had not been administered;
wherein an increased age of appearance of the trait in the first mouse compared to that in the second mouse indicates efficacy of the compound.

In accordance with a further embodiment, a method is provided for screening a candidate compound for its efficacy in ameliorating the symptoms of Alzheimer's Disease, the method comprising the steps of:
(a) administering the candidate compound to a first transgenic mouse as described herein;
(b) determining the performance of said mouse in a memory or learning test; and
(c) comparing the performance of said mouse with the performance of a second transgenic mouse of the same type to which the compound has not been administered;
wherein an improved performance of the first mouse compared to that of the second mouse indicates efficacy of the compound.

In accordance with a further embodiment, a method is provided for producing a transgenic non-human mammal that displays abnormal Aβ deposition in its central nervous system comprising:
(a) introducing into a fertilized oocyte of said mammal a transgene comprising a nucleotide sequence operably linked to a promoter and encoding a heterologous amyloid precursor protein 695 ($APP_{695}$) polypeptide wherein the lysine residue at position 670 is substituted by asparagine, the methionine residue at position 671 is substituted by leucine and the valine residue at position 717 is substituted by phenylalanine;
(b) transplanting said fertilized oocyte into a pseudopregnant mammal;
(c) allowing said fertilized oocyte to develop into a live born offspring; and
(d) selecting an offspring whose genome comprises a transgene comprising a nucleotide sequence operably linked to a promoter and encoding a heterologous amyloid precursor protein 695 ($APP_{695}$) polypeptide wherein the lysine residue at position 670 is substituted by asparagine, the methionine residue at position 671 is substituted by leucine and the valine residue at position 717 is substituted by phenylalanine and wherein the transgene is expressed.

In accordance with a further embodiment is provided a nucleotide sequence encoding a heterologous amyloid precursor protein 695 ($APP_{695}$) polypeptide wherein the lysine residue at position 670 is substituted by asparagine, the methionine residue at position 671 is substituted by leucine and the valine residue at position 717 is substituted by phenylalanine. Also provided is a vector comprising such a nucleotide sequence operably linked to a promoter.

Certain embodiments of the invention are described, below:

The TgCRND8 mice (n=5) had significantly longer escape latencies and search paths than their non-Tg littermates (n=8), ($F(1,10)=28.8$, $p<0.001$ and $F(1,10)=22.0$, $p<0.01$, respectively), and consequently dwelled significantly less ($F(1,10)=14.9$, $p<0.01$) in the target quadrant (TQ) containing a hidden platform. The locomotor abilities assessed by the speed of swimming between Tg and non-Tg mice were comparable ($F(1,10)=0.48$, $p>0.05$).

The TgCRND8 mice showed impaired spatial memory for the platform position as measured by their search patterns during 60 seconds swim in the probe trial when the hidden platform was removed from the pool. They showed a tendency to search the TQ less and crossed the exact annulus of the platform position significantly less often ($t(10)=2.1$, $p=0.06$) than non-Tg mice.

The water-maze performance of bi-transgenic TgCRND8×TgPS2(M239V)1379 mice was tested. When tested at 2 months of age, the bi-transgenic mice (n=5) had significantly longer ($F(1,11)=8.1$, $p<0.05$, with the effect size due to the genotype ($\eta^2$)=42%) escape latencies and the search path($F(1,1 1)=8.46$, $p<0.05$, $\eta^2=43\%$), than the single Tg PS2(M239V)1379 littermates (n=8). During immediately following learning reversal test when the hidden platform was moved to the opposite quadrant to the original TQ, the bi-transgenic mice showed a tendency to longer escape latencies ($F(1,11)=3.28$, $p=0.1$, $\eta^2 23\%$ but their search paths did not differ significantly from the single TgPS2(M239V) 1379 mice ($F(1,11)=2.46$, $p>0.05$, $\eta^2=18\%$). The swim speed of the mice in both transgenic groups was comparable during the tests.

When re-tested at 5 months of age, the bi-transgenic mice showed significantly longer ($F(1,10)=16.6$, $p<0.01$, $\eta^2=62\%$, (1 bi-transgenic mouse died)) escape latencies and significantly longer search paths ($F(1,10)=20.3$, $p<0.001$, $\eta^2=66\%$ than the single Tg PS2(M239V)1379 littermates. This significant impairment was due to the initial poor performance of bi-transgenic mice in the tests (group×days interactions: $F(2,40)=3.32$, $p<0.05$ for latency and $F(2,40)=2.85$, $p=0.07$ for path) This impairment in learning acquisition persisted in the reversal tests when the bi-transgenic mice still showed significantly longer latencies ($F(1,10)=28.58$, $p<0.001$, $\eta^2=74\%$ and longer search paths ($F(1,10)=27.43$, $p<0.001$, $\eta^2=73\%$ then single Tg littermates. Although the mice eventually improved their performance at the end of learning reversal training, the group×days interactions for both measures did not reach significance at $\alpha=0.05$.

The water maze performance of TgCRND8 mice (Tg (APP)8); n=12) and non-transgenic littermates (non-Tg; n=20) immunised with Aβ42 and TgCRND8 mice (Tg(APP) 8; n=9) and non-transgenic littermates (non-Tg;n=19) immunised with IAPP-peptide was tested. The immunisation with the $A\beta_{42}$ peptide significantly reduced cognitive deficit in TgCRND8 mice as measured by their escape latency and the search path as compared to non-Tg littermates. Although the Aβ42-immunised TgCRND8 mice showed overall longer escape latencies and search paths, ($F(1,30)=9.71$, $p<0.01$; $F(1,30)=10.9$, $p<0.01$ for latency and path respectively) than non-Tg mice, the difference was due to their initial longer searches (group×day interactions: $F(4,120)=2.83$, $p<0.05$-latency; $F(3,120)=4.73$, $p<0.01$-path). The comparisons of their performance during the last 3 days of training did not reveal significant differences between the groups ($F(1,30)=0.64$, $p>0.05$-latency; $F(1,30)=1.24$, $p>0.05$-path). The Aβ42-immunised Tg mice showed a slight tendency to search the TQ less ($F(1,30)=3.71$, $p=0.06$), but their swim speed did not differ significantly from non-Tg mice ($F(1,30)=1.33$, $p>0.05$).

The IAPP immunised TgCRND8 mice showed significantly longer escape latencies and search paths than their non-Tg littermates ($F(1,26)=39.9$, $p<0.001$-latency; $F(1,26)=43.9$, $p<0.001$-path). Although they did not differ in their initial search from nonTg mice, they did not improve their performance during training (group×day interactions: $F(4,104)=6.31$, $p<0.001$-latency, $F(4,104)=5.69$, $p<0.001$-path). They also spent significantly less time searching the target quadrant ($F(1,26)=7.39$, $p<0.05$), but their swim speed was not affected by the immunisation ($F(1,26)=1.73$, $p>0.05$).

DETAILED DESCRIPTION OF THE INVENTION

The invention provides a transgenic non-human mammal, preferably a rodent, and more preferably a mouse, which displays abnormal Aβ deposition similar to that seen in a number of human disorders such as Alzheimer's Disease (AD), Lewy Body variant of Alzheimer's Disease, and certain types of Creutzfeld-Jacob Disease (CJD), which cause dementia, and hereditary cerebral angiopathy with amyloidosis-Dutch type (HCAWA-D) and senile amyloid angiopathy which cause cerebral hemorrhage.

The non-human transgenic mammal of the invention shows both histological and behavioural deficits as a result of the abnormal Aβ deposition. In particular, the transgenic non-human mammal of the invention displays an accelerated appearance of various facets of human AD-related pathology and provides an improved animal model of AD.

In accordance with one embodiment, the non-human mammal of the invention comprises a mammal having in its genome a transgene encoding a heterologous $APP_{695}$ polypeptide, preferably a human $APP_{695}$ polypeptide, carrying both the "Swedish" mutation and the "Indiana" mutation of Alzheimer amyloid precursor protein (APP). Both of these mutations are associated, in humans, with Familial Alzheimer's Disease (FAD).

In accordance with a preferred embodiment, the invention comprises a transgenic mouse designated TgCRND8 which has an $APP_{695}$ transgene which carries both the "Swedish" mutation and the "Indiana" APP mutations.

Transgene constructs were based upon a cDNA cassette encoding the major APP isoform in human brain, $APP_{695}$. This cassette was modified to include two FAD mutations: the "Swedish" mutation (K670N, M671L) and the "Indiana" mutation (V717F), lying adjacent to the N- and C-terminal boundaries of the APP Aβ domain. The cassette was introduced into cosTet, a prion promoter expression vector which directs position-independent transgene expression in CNS neurons, and to a lesser extent astrocytes. Microinjections were carried out into oocytes of a hybrid genetic background, including C3H and C57BL6 strains. The resulting transgenic mouse line was designated TgCRND8.

As will be understood by those of ordinary skill in the art, any promoter may be used which directs central nervous system or neuronal expression of the transgene. These include the neuron specific enolase gene promoter (37); the human platelet derived growth factor B subunit promoter (38), the Thy-1 promoter (19) and the neurofilament promoter (41).

The expression cassette preferably includes promoter and locus control region sequences from a gene which is expressed in the brain and preferably which is expressed at a level in proportion to the number of transgene copies incorporated into the genome.

The use of a double-cis mutant $APP_{695}$ transgene cassette has not been previously reported; other AD models have used $APP_{751}$ (KM670/671NL+V7171)(19) or $APP_{770}$ (KM670/671NL+V717F) (27) transgenes).

TgCRND8 mice exhibit profuse CNS amyloid deposits in the form of spherical plaques immunoreactive for Aβ peptide as early as 90 days after birth; such plaques are characteristic of human AD. Isolated plaque deposits are visible in TgCRND8 mice as early as 66 days after birth. The appearance of amyloid deposits in TgCRND8 mice occurs earlier than in any previously reported animal model of AD employing single transgenes (see Table 1).

A review of murine models of Alzheimer's Disease has been published (16) and some examples are listed in Table 1. As noted from the listed properties, the TgCRND8 mice represent an unexpected and substantial improvement over other currently available animal models of AD.

For example, the previously described double-cis mutant APP transgene model, the "TgAPP22" mouse, which employed a double-mutant $APP_{751}$ cassette (KM670/671NL+V7171), showed the appearance of Aβ plaques at 18 months of age (19) and the J9 line, a double-mutant $APP_{770}$ cassette (KM670/671NL+V717F), was reported to develop plaques at 8-10 months (27).

The previously reported bi-transgenic mouse, Tg2576× TgPS1, had minimal plaque deposits in the cingulate cortex from 70 days of age (39) but eventually showed well-formed deposits at 6 months (22).

The TgCRND8 mouse is useful for the discovery and development of diagnostics and therapeutic compounds for treatment of AD, as well as for the better elucidation of the pathogenic mechanisms of the disease.

TgCRND8 mice exhibit deficits in spatial learning, as assessed by the hidden-platform version of the Morris water-maze. These deficits, measured against control non-transgenic littermates, can be detected as early as 11 weeks of age.

The inventors have also shown that immunization of TgCRND8 mice with human Aβ$_{42}$peptide, using the protocol of Schenk et al. (26), results in significant improvement in both behaviour and in neuropathology at 10-22 weeks of age, as described in Example 5. In contrast, the PDAPP mice used by Schenk et al have only been shown to exhibit an improvement in neuropathology but not in behaviour (26).

The TgCRND8 model is thus the first AD animal model in which modulation of Aβ deposition (a known and widely accepted initiating event in Alzheimer's Disease) has been shown to lead to amelioration of both pathology and behaviour, thus providing the most appropriate model to date for testing new therapies and for screening candidate therapeutic compounds.

Such therapies or compounds might be aimed at inhibiting the function of PS1 in γ-secretase cleavage of βAPP or at accelerating removal of proteolytic derivatives of βAPP. These proteolytic APP derivatives include Aβ itself, which is known to be neurotoxic in aggregated forms, as well as the C-terminal derivatives resulting from γ-secretase cleavage of α-and β stubs (C83/C99-βAPP) which have been suggested to be neurotoxic (25).

The transgenic mice of the invention are also useful for the development of new diagnostics. For example, putative assays of cerebral Aβ load or tests for neuronal injury in response to Aβ accumulation may be carried out with the transgenic mice described herein.

The transgenic non-human mammals of the invention, having a transgene encoding $APP_{695}$ with both the Swedish and Indiana mutations, may be crossed with other lines of the mammal which bear a different mutation, either in a transgene or in an endogenous gene, to produce a "bi-transgenic mammal".

A "bi-transgenic mammal" as used herein means a mammal whose genome comprises a transgene comprising a nucleotide sequence encoding a heterologous $APP_{695}$ polypeptide, preferably a human $APP_{695}$ polypeptide, carrying the Swedish and Indiana APP mutations and a selected second gene, preferably a gene comprising a nucleotide sequence encoding a protein having at least one selected mutation.

The second gene may be an endogenous gene bearing the at least one selected mutation, or a homologous or heterologous transgene bearing the at least one selected mutation. The selected mutation may be, for example, an AD-related mutation or a mutation in a gene related to Aβ processing.

Alternatively, the selected second gene may be a normal transgene.

The TgCRND8 mice described herein are useful for the creation of further AD animal models, in that the pathway for accelerated synthesis of Aβ peptide is not saturated in these mice, allowing them to be crossed with other transgenic mice to give bi-transgenic models with further enhancements of the AD-related pathological process of amyloid peptide synthesis and deposition.

TgCRND8 mice may be crossed, for example, with transgenic animals bearing a mutant presenilin gene, a mutant APOE4 gene, a mutant nicastrin gene or a different mutant of an APP gene.

In accordance with a preferred embodiment, the invention provides bi-transgenic mice produced by crossing a TgCRND8 mouse with (a) a transgenic mouse comprising a transgene encoding a mutant presenilin 1 protein, preferably a PS1 (L286V) presenilin 1 protein;

(b) a transgenic mouse comprising a transgene encoding a mutant presenilin 2 protein, preferably a PS2 (M239V) presenilin 2 protein, or (c) a transgenic mouse comprising a transgene encoding a presenilin 1 protein having two mutations, preferably a PS1 (M146L+L286V) presenilin 1 protein.

The first generation offspring produced by the crossing are screened, using conventional methods, for the presence and expression of both the first and second transgenes, to select bi-transgenic mice.

TgCRND8 mice may also be crossed with transgenic animals bearing a mutation in a gene related to Aβ processing, such as a low density lipoprotein receptor related gene, an α2-macroglobulin gene or a β-secretase gene.

TgCRND8 mice were crossed with transgenic mice which over-express mutant human presenilin (PS1 or PS2) transgenes (Table 2). A potent increment in plaque density was noted in TgCRND8 mice which co-express a human mutant presenilin transgene denoted TgPS1(L286V)1274 (which carries a familial Alzheimer disease (FAD) mutation). Thus, in TgCRND8×TgPS1(L286V)1274 mice, an amyloid burden closely resembling the postmortem AD brain is already present by 62 days of age.

In a similar manner, crossing TgCRND8 mice with mice carrying the FAD mutant form of presenilin 2 (a methionine to valine mutation at amino acid residue 239 of the PS2 gene coding region) also results in a potent increment in plaque density.

A still greater enhancement was obtained by crossing TgCRND8 mice with mice bearing a human mutant presenilin transgene with two FAD mutations in cis to each other-denoted Tg(M146L+L286V)6500. In TgCRND8× TgPS1(M146L+L286V)6500 mice, hippocampal amyloid deposits were detectable by 30 days of age, which is 5 months earlier than previously reported for any other double APP/PS 1-Tg mice (which typically develop plaques at or after 6 months of age) (22, 23).

All of these bi-transgenic mice showed an even more accelerated appearance of hippocampal amyloid plaques, compared with either the TgCRND8 parent or the TgPS1 parent (Table 2).

In addition to accelerated appearance of AD-related features compared with previously described Tg mice, preliminary analyses indicate that a substantial loss of cortical neurons is evident in 43 day-old TgCRND8×TgPS1 (M146L+L286V)6500 bi-transgenic mice.

A progressive deterioration in cognitive performance beginning at age 8-10 weeks has also been seen in bi-transgenic mice generated by crossing TgCRND8 mice with mice expressing an FAD allele of presenilin 2 (TgPS2 (M239V), line 1379.

The TgCRND8 mice described herein, and crosses of these mice with other mouse lines bearing a selected mutation, for example an AD-related mutation, as further described herein, are useful for a number of purposes.

These mice may be used to screen potential pharmaceutical compounds for their efficacy in preventing or delaying the development of any of the pathological indicia, for example the AD-related phenotypic traits, seen in these mice. There is thus provided a method for screening candidate compounds for their efficacy in preventing or delaying the development of AD. The screening method comprises administering a candidate compound to a transgenic mouse of the invention prior to the appearance of a selected AD-related phenotypic trait, and comparing the age at which the selected phenotypic trait appears in the treated mouse to the age of appearance of that trait in untreated transgenic mice. Suitable AD-related traits to examine would include appearance of abnormal brain histology or appearance of behavioural deficits. Behavioural deficits may be determined, for example, by examining the performance of the mice in a memory or learning test such as the water maze test, as described herein.

These mice can also be used to screen potential pharmaceutical compunds for their efficiency in ameliorating the symptoms of AD by similarly administering and comparing the effects of candidate compounds in transgenic animals after appearance of a selected AD-related trait, such as abnormal brain histology or a behavioural deficit.

The specific etiology of the disease can be identified during growth and development of the transgenic animal to study the disease progression and effects both physiologically and physically. Transgenic animals of the present invention which in a short time rapidly overexpress Aβ in the brain can now be made and studied and used as a model to study possible therapies including pharmaceutical intervention, gene targeting techniques, antisense therapies, antibody therapies etc. Furthermore, transgenic in vitro cell lines can also now be established in accordance with the lo present invention and also used in order to elucidate intracellular signalling systems involved in the disease as well as test and identify potentially therapeutic compounds.

Furthermore, the transgenic mammals of the present invention can also be used to examine situations or environmental hazards which are suspected of accelerating or initiating Alzheimer's Disease, such as for example, head trauma or toxic environmental agents. In this case, the transgenic mammal may be exposed to a particular situation and then observed to determine neurobehavioral decline, premature death, gliosis, etc. as indicators of the capacity of the situation to further provoke and/or enhance AD.

The transgenic mammals of the present invention are useful for the more detailed characterization of Alzheimer's Disease to lead to elucidation of the pathogenesis of the progressive neurologic pathology and determination of the sequence of molecular events. The transgenic mammals are useful for studying various proposed mechanisms of the pathogenesis of the disease in order to lead to better treatments for the disease.

The transgenic mice of the invention are also useful for the identification of previously unrecognized genes which may also play a role in AD, either beneficial or deleterious. A transgenic mouse bearing a candidate gene is crossed with a transgenic mouse of the invention and the effect of the presence of the candidate gene on the AD-related traits of the transgenic are examined. A candidate gene will be scored as beneficial if it delays or dilutes AD-related phenotypes such as amyloid deposition and impaired cognitive performance. Conversely, a candidate gene will be scored as favouring the development of AD if it advances the age of onset or enhances the penetrance of AD-related phenotypes such as amyloid deposition and impaired cognitive performance.

Additionally, the transgenic mice of the invention are useful for testing possible gene therapies for familial AD, for example gene therapy by administration of additional copies of a normal presenilin gene.

It will be understood by those skilled in the art that the present invention is not limited to production of transgenic mice and provides non-human animal models of human Alzheimer's Disease. Such models provide for the identification of the role of βAPP and Aβ peptide during embryogenesis, growth and development and for the understanding of the function of βAPP and Aβ peptide as involved in Alzheimer's Disease.

Mice are often used for transgenic animal models because they are easy to house, relatively inexpensive, and easy to breed. However, other non-human transgenic mammals may also be made in accordance with the present invention such as, but not limited to, monkeys, sheep, rabbits and rats. Transgenic animals are those which carry a transgene, that is, a cloned gene introduced and stably incorporated which is passed on to successive generations. In the present invention, the human $APP_{695}$ cDNA was cloned and modified to contain two FAD mutations, the "Swedish" (K670N, M671L) and the "Indiana" mutation (V717F). This construct was then stably incorporated into the genome of a mouse.

There are several methods by which to create a transgenic animal model carrying a certain gene sequence in addition to that specifically described herein.

Generation of a specific alteration/mutation of the human APP gene sequence is one strategy. Alterations can be accomplished by a variety of enzymatic and chemical methods used in vitro. One of the most common methods is using a specific oligonucleotide as a mutagen to generate precisely designed deletions, insertions and point mutations in a DNA sequence. Secondly, a wild type human gene and/or humanized murine gene could be inserted by homologous recombination. It is also possible to insert an altered or mutant (single or multiple) human gene as genomic or minigene constructs using wild type or mutant or artificial promoter elements. Knock-out of the endogenous murine genes may be accomplished by the insertion of artificially modified fragments of the endogenous gene by homologous recombination. In this technique, mutant alleles are introduced by homologous recombination into embryonic stem cells. The embryonic stem cells containing a knock out mutation in one allele of the gene being studied are introduced into early mouse embryos. The resultant mice are chimeras containing tissues derived from both the transplanted ES cells and host cells. The chimeric mice are mated to assess whether the mutation is incorporated into the germ line. Those chimeric mice each heterozygous for the knock-out mutation are mated to produce homozygous knock-out mice.

Gene targeting producing gene knock-outs allows one to assess in vivo function of a gene which has been altered and used to replace a normal copy. The modifications include insertion of mutant stop codons, the deletion of DNA sequences, or the inclusion of recombination elements (lox p sites) recognized by enzymes such as Cre recombinase. Cre-lox system allows for the ablation of a given gene or the ablation of a certain portion of the gene sequence.

To inactivate a gene, chemical or x-ray mutagenesis of mouse gametes can be applied, followed by fertilization. Heterozygous offspring can then be identified by Southern blotting to demonstrate loss of one allele by dosage, or failure to inherit one parental allele using RFLP markers.

To create a transgenic mouse, an altered version of the human gene of interest can be inserted into a mouse germ line using standard techniques of oocyte microinjection or transfection or microinjection into stem cells. Alternatively, if it is desired to inactivate or replace the endogenous gene, homologous recombination using embryonic stem cells may be applied as described above.

For oocyte injection, one or more copies of the altered/mutated human APP gene sequence can be inserted into the pronucleus of a just-fertilized mouse oocyte. This oocyte is then reimplanted into a pseudo-pregnant foster mother. The liveborn mice can then be screened for integrants using analysis of tail DNA for the presence of the altered APP gene sequences. The transgene can be either a complete genomic sequence injected as a YAC or chromosome fragment, a cDNA with either the natural promoter or a heterologous promoter, or a minigene containing all of the coding region and other elements found to be necessary for optimum expression.

Retroviral infection of early embryos can also be done to insert the altered gene. In this method, the altered gene is inserted into a retroviral vector which is used to directly infect mouse embryos during the early stages of development to generate a chimera, some of which will lead to germline transmission.

Homologous recombination using stem cells allows for the screening of gene transfer cells to identify the rare homologous recombination events. Once identified, these can be used to generate chimeras by injection of mouse blastocysts, and a proportion of the resulting mice will show germline transmission from the recombinant line. This gene targeting methodology is especially useful if inactivation of the gene is desired. For example, inactivation of the gene can be done by designing a DNA fragment which contains sequences from an exon flanking a selectable marker. Homologous recombination leads to the insertion of the marker sequences in the middle of an exon, inactivating the gene. DNA analysis of individual clones can then be used to recognize the homologous recombination events.

It is also possible to create mutations in the mouse germline by injecting oligonucleotides containing the mutation of interest and screening the resulting cells by PCR.

One skilled in the art would readily comprehend that the nucleic acid construct as used to produce the transgenic mammals of the invention may contain any suitable nucleic acid sequence which encodes the mutant $APP_{695}$ protein which leads to increased Aβ production in the brain. Such nucleic acid sequence is preferably the full-length mutated $APP_{695}$ cDNA, but may encompass other altered derivatives of such sequence so long as the desired mutant form of the protein is expressed and Aβ production is markedly increased.

EXAMPLES

The examples are described for the purposes of illustration and are not intended to limit the scope of the invention.

Methods of synthetic chemistry, protein and peptide biochemistry, molecular biology, histology and immunology referred to but not explicitly described in this disclosure and examples are reported in the scientific literature and are well known to those skilled in the art.

Example 1

TgCRND8 Transgenic Mice

A human β-Amyloid Precursor Protein(1) (βAPP) cDNA cassette comprising 90 base-pairs of 5' untranslated region, a 695 amino acid residue coding region ("APP695"), and 271 bp of 3' untranslated region was mutagenized to introduce, in cis to each other, two mutations associated with familial Alzheimer's Disease (FAD). The first mutation was the "Swedish" mutation (2), a dinucleotide change affecting two adjacent codons (KM670/671NL: GA->TC at nucleotides 1785 and 1786, using the codon/nucleotide numbering of the APP770 transcript (1)). The second mutation was a single nucleotide change producing the V717F substitution (3) (G->T at nucleotide 1924, using codon/nucleotide numbering of the APP770 transcript (1)). The APP695 transcript, which lacks exons 7 and 8 encoding the Kunitz Protease Inhibitor domain, is the principal transcript expressed in brain. The βAPP double-mutant cDNA cassette was inserted into the prion protein cosmid expression vector cosTet. (10)

The resulting recombinant cosmid clone was expanded in culture, lysed to yield supercoiled DNA, and the mammalian DNA insert comprising the PrP gene regulatory elements and the APP coding region excised from the prokaryotic vector sequences in this molecular clone by digestion with the restriction endonuclease Not1. Subsequent to agarose gel electrophoresis to purify this transgene Not 1 DNA fragment, purified DNA was microinjected into fertilized mouse oocytes (deriving from mating (C3H×C57BL6)× mice), using standard protocols.(29) Following implantation into foster mothers, transgene positive offspring among live births were screened by hybridization analysis of tail DNA, using a DNA probe fragment derived from the 3' untranslated region of the Syrian hamster PrP gene.(30)

APP-specific antibodies (Senetek Inc., Boehringer-Mannheim) were used to establish transgene expression in transgene positive offspring. 10% brain homogenates made in 0.32M sucrose were diluted with Laemlli buffer, sonicated and run on 10-20% tricine gradient gels (Novex). Following transfer to nitrocellulose, human APP and PS1 were detected using C- and N-terminal specific Mab's and developed by ECL (Amersham). The results are shown in FIG. 6. In addition to full-length mature and immature APP holoprotein of 120 and 100 kDa, western blot analyses revealed lower molecular weight species in brain extracts of TgCRND8 mice, with lower levels of APP expression. Detection of these species with 6E10 antiserum (positioned N-terminal to the α-secretase cleavage site) and antibody 369 indicates that these derive from the C-terminus of APP. These were likely APP processing intermediates that accumulated to high levels by virtue of overexpression, and correspond to C-terminal fragments (CTFs) commencing at the β-secretase site (so-called β-stubs). In aged TgCRND8 mice, but not age-matched non-Tg littermates or Tg2576 mice, increasing levels of 4 kDa species were also detected as animals aged. The 4 kDa immunoreactive species correspond to the Aβ peptide, which accumulates to high levels during the lifetime of these animals.

Microinjection of DNA transgenes into oocytes, as described above, leads to insertion of the transgenes at random into the mouse genome. Restriction endonuclease mapping of inserted transgenes demonstrates that they are inserted in head-to-tail arrays, with the number of transgenes per array (copy number) reaching up to more than 100 transgene copies per haploid genome (24).

Transgenic mice expressing human APP should show overexpression of APP, preferably 5 to 6 times the endogenous expression level, for optimum amyloidogenesis. APP expression in brain is determined by western blot analysis using an APP-directed antibody such as 22C11 (Roche Diagnostics) which recognises both mouse and human APP.

Previous work on the prion protein cos.Tet vector has shown position-independent expression of transgene arrays, such that transgene expression levels rise in parallel with copy number (4, 40). When this vector is used, transgenic mice with the desired high level of APP expression can therefore be first identified by identifying, by hybridization analysis (30) transgene-positive mice with a high transgene copy number, preferably at least 30 copies.

Although mice containing the FVB/N genetic background are prone to premature death in early adult life, attributed to a poorly-defined effect of APP overexpression, this tendency is attenuated in a genetic background derived from C57 and C3H strains. The TgCRND8 mice therefore establish that levels of Aβ peptide can be tolerated without compromising viability.

Neuropathological Changes in TgCRND8 Mice

Immunostaining was performed using the human specific antibody 4G8, which reacts with the Aβ proteolytic fragment of APP, using sections from formalin-fixed, paraffin wax embedded brain material. Standard protocols for this immunohistochemical procedure have been described elsewhere (17,20, 23). Isolated plaque deposits first became visible in TgCRND8 mice as early as 60 days after birth, with robust deposition of diffuse amyloid plaques from 90 days of age. Dense-cored plaques plaques were apparent by 4-5 months of age, with many of these types of deposits staining with Congo Red (a reagent that intercalates into β-sheet rich amyloid deposits) to yield green/gold birefringence under polarized light. Similar birefringent deposits are present in human AD brain samples. Amyloid deposits were prominent in the hippocampus and cerebral cortex (especially in the frontal cortex) of TgCRND8 mice, areas heavily affected by Alzheimer's Disease in humans. The cerebellum, which is usually spared in sporadic AD, but which can be mildly affected by diffuse Aβ deposits in severe early-onset cases of AD, is also mildly affected in one year old TgCRND8 mice and in TgCRND8 mice co-expressing mutant PS1 or PS2 at 6 months of age.

Though the APP was expressed systemically in TgCRND8 mice, (as is the hamster PrP gene), amyloid deposits were not apparent by immunostaining in the kidney, skeletal muscle, and cardiac muscle of aged animals with florid CNS deposition, even though these are known sites of PrP mRNA expression.

Behavioural Changes in TgCRND8 Mice

Spatial learning was assessed in TgCRND8 mice using a well-established paradigm, the Morris water maze (31) as described (32). The analysis of behaviour of TgCRND8 mice revealed a significant cognitive deficit in their acquisition of spatial information assessed in the place discrimination (hidden platform in the same spatial position) version of a water maze as early as 11 weeks of age. During training, the mice showed a significantly slower learning rate reflected by their longer escape latencies and search paths as well as chance level search of the quadrant containing the hidden platform. The TgCRND8 mice also showed spatial memory deficit when tested in the probe trail. During this trial, the hidden platform was removed and mice were allowed to search for its position for 60 seconds. While the non-Tg mice showed clear, selective spatial bias for the platform position, the search of TgCRND8 mice was more generalised and included adjacent to TQ quadrants, and crossed the annulus of the platform position significantly less then non-Tg littermates. The swimming abilities of both APP positive and non-Tg mice were comparable during testing, thus did not bias the measures of learning.

Example 21

TgCRND8×TgPS1 (L286V) 1274 bi-transgenic Mice

TgCRND8 mice were mated with transgenic mice bearing an FAD-related mutant presenilin 1 gene, designated TgPS1 (L286V) line 1274, their progeny were weaned, and tail biopsies removed for the preparation of genomic DNA. Purified tail DNAs were immobilized in duplicate "dot-blot" arrays on a Nylon membrane and hybrized to using a human APP coding region gene-specific probe excised from a cDNA clone or a human PS1 cloning region probe fragment excised from a cDNA clone. These DNA restriction fragments were labeled by random priming with α-32p-dCTP (33). The duplicate Nylon membranes were incubated with either APP or PS1 hybridization probes, and washed in a solution of 0.1% sodium dodecyl suphate, 0.1×saline sodium citrate at a temperature of 65° C. (this corresponds to a "stringent" post-hybridization wash such that signals deriving from endogenous PS1 and APP genes in the mouse genome are minimized). Bi-transgenic mice were identified by virtue of the fact that the corresponding tail DNA samples hybridized to both the APP and the PS1 gene-specific probes.

Neuropathological Changes in TgCRND8×TgPS1 (L286V)1274 Bi-transgenic Mice

Amyloid deposition was enhanced in the resulting bi-transgenic mice, these mice showing an amyloid burden closely resembling the post mortem human AD brain by 62 days of age.

In aged mice, amyloid deposition was sufficiently florid that it extended to structures usually spared in single-transgenic mice (e.g., cerebellum).

Example 3

TgCRND8×TgPS2(M239V) 1379 Bi-transgenic Mice

TgCRND8 mice were also crossed with the transgenic line designated TgPS2(M239V) line 1379, which expressed a mutant presenilin 2 allele in the context of the same prion protein cosmid expression vector cosTet. Bi-transgenic TgCRND8×TgPS2(M239V)1379 mice were genotyped as described above for TgCRND8×TgPS1(L286V)1274 mice, with the exception that a PS2 coding region DNA hybridization probe was used in place of a PS1 coding region hybridization probe.

These bi-transgenic mice exhibited profuse CNS amyloid deposits in the form of spherical plaques immunoreactive for Aβ peptide by 91 days after birth. These amyloid deposits were located in the hippocampus and cerebral cortex, areas heavily affected by Alzheimer's Disease in humans. The cerebellum is usually affected by diffuse Aβ deposits only in severe early-onset cases of Alzheimer's Disease; it is affected in mice with the very heaviest plaque burdens.

Behavioural Changes in TgCRND8×TgPS2(M239V)1379 Bi-transgenic Mice

TgCRND8 ×TgPS2(M239V)1379 bi-transgenic mice were tested at 2 months of age and showed a significant cognitive defect in spatial learning acquisition with the effect size in the range of 40%. During the following reversal test, however, although inferior at the beginning, the bi-transgenic mice showed comparable performance by the end of the test (about 20% of variance explained by the trans-genotype). During the re-test at 5 months of age, the same bi-transgenic mice showed highly significant learning deficit during acquisition and reversal test (effect size due to transgenotype of 60% and 70% respectively). Also, the bi-transgenic mice did not differ from TgPS2(m239V)1379 mice in their swim speed at any age tested. Expression of mutated human APP in the presence of mutated PS2 gene confers impairment in spatial learning and memory as early as 2 months of age, as compared to the performance of TgPS2(M239V)1379 mice which behave in a manner similar to non-transgenic mice derived from the same combination of inbred strains. This impairment progresses with age and by the age of 5 months, the mice show constant deficiency in acquiring new spatial information.

Example 4

TgCRND8×Tg(M146L+L286V) 6500 Bi-transgenic Mice

TgCRND8 mice were crossed with transgenic mice bearing two mutations of PS1 (M146L+L286V) (34) The PS1 double mutant mice were created by standard procedures, as described previously (35). Bi-transgenic mice were identified by genotype analysis of tail DNA by hybridization with two independent DNA probes, as described above for TgCRND8×TgPS1(L286V) 1274 bi-transgenic mice.

The resulting double bi-transgenic mice showed punctate AB amyloid deposits in the cortex by one month of age, with multiple diffuse AB amyloid plaques present by 43 days of age. Some of the plaques apparent at age 43 days were congophilic (i.e. can be stained with the Congo Red reagent).

Example 5

Active Immunization Against Aβ Alters Cognitive Deficits in TgCRND8 Mice

A group of TgCRND8 mice and a group of non-transgenic littermates were immunized with synthetic Aβ42 peptide as described by Schenk et al.(36). Control groups of TgCRND8 mice and non-transgenic littermates were immunised with a control amyloidogenic peptide (islet amyloid polypeptide (IAPP), which is associated with the pathogenesis of diabetes). The performance of these two transgenic groups in the water maze test, as described above, was compared with the performance of the non-Tg littermates. The results are shown in FIG. 3.

Immunisation with Aβ42 peptide attenuated the cognitive impairment of TgCRND8 mice at early stages of immunisation. The water maze performance of TgCRND8 mice inimunised with $Aβ_{42}$ or 1APP (immunisation commenced at 6 weeks of age) was tested at 11 weeks of age. The immunisation with the $Aβ_{42}$ peptide significantly reduced cognitive deficit in TgCRND8 mice as measured by escape latency and search path length as compared to non-Tg littermates. Although the Aβ42 immunised TgCRND8 mice showed overall longer escape latencies and search paths, ($F(1,30)$9.71, $p<0.01$; $F(1,30)=10.9$, $p<0.01$ for latency and path respectively), than non-Tg mice, the difference was due to their initial longer searches (group×day interactions: $F(4,120)-2.83$, $p<0.05$-latency; $F(3,120)=4.73$, $p<0.01$-path). The comparisons of their performance during the last 3 days of training did not reveal significant differences between the groups ($F(1,30)=0.64$, $p>0.05$-latency; $F(1,30)=1.24$, $p>0.05$-path). The Aβ42 immunised TgCRND8 mice showed a slight tendency to search the TQ less ($F(1,30)=3.71$, $p=0.06$, but their swim speed did not differ significantly from non-Tg mice ($F(1,30)=1.33$, $p>0.05$). The IAPP immunised TgCRND8 mice showed significantly longer escape latencies and search paths than their non-Tg littermates ($F(1,26)=39.9$, $p<0.001$-latency; $F(1,26)=43.9$, $p<0.001$-path). Although the transgenics did not differ in their initial search from nonTg mice, they did not improve their performance during training (group×day interactions: $F(4,104)=6.31$, $p<0.001$-latency, $F(4,104)=5.69$, $p<0.001$-path). They also spent significantly less time searching the target quadrant ($F(1,26)=7.39$, $p<0.05$), but their swim speed was not affected by the immunisation ($F(1,26)=1.73$, $p>0.05$).

In summary, the immunisation of TgCRND8 mice with Aβ42 peptide at 6 weeks followed by a boost at 8 weeks, significantly improved the cognitive abilities of TgCRND8 mice in the water maze paradigm administered at 11 weeks of age. On the other hand, the mice immunized with IAPP showed significant impairment in acquisition of spatial information as compared to non-Tg littermates, and this impairment was of a similar nature to that seen in non-immunised TgCRND8 mice.

Immunisation with Aβ42 or IAPP peptides did not affect swimming abilities of the mice. These findings indicate that immunisation with Aβ42 (but not the control IAPP peptide) improves performance in the water maze, and that this improvement can occur at a time coincident with the first deposition of Aβ amyloid plaques in the hippocampus. These findings also establish that the cognitive impairment in TgCRND8 is not due to an irreversible congenital defect.

The present invention is not limited to the features of the embodiments described herein, but includes all variations and modifications within the scope of the claims.

REFERENCES

1. Kang, J., Lemaire, H. G., Unterbeck, A., Salbaum, J. M., Masters, C. L., Multhap, G., Beyreuther, K., Muller-Hill, B. (1987) The precursor of Alzheimer disease amyloid A4 protein resembles a cell surface receptor. *Nature*, 325: 733-736.
2. Mullan, M. J., Crawford, F., Axelman, K., Houlden, H., Lilius, L., Winblad, B., Lannfelt, L., and Hardy, J. (1992) A pathogenic mutation for probable Alzheimer's Disease in the APP gene at the N-terminus of B-amyloid. *Nature Genetics*, 1: 345-347.
3. Murrell, J., Farlow, M., Ghetti, B., and Benson, M. D. (1991) A mutation in the amyloid precursor protein associated with hereditary Alzheimer's Disease. *Science*, 254: 97-99.
4. Citron, M., Oltersdorf, T., Haass, C., McConlogue, C., Hung, A. Y., Seubert, P., Vigo-Pelfrey, C., Lieberburg, I., and Selkoe, D. J. (1992) Mutation of the B-amyloid precursor protein in familial Alzheimer's Disease increases B-protein production. *Nature*, 360: 672-674.
5. Citron, M., Vigo-Pelfrey, C., Teplow, D. B., et al. (1994) Excessive production of amyloid B-protein by peripheral cells of symptomatic and presymptomatic patients carrying the Swedish Familial Alzheimer's Disease mutation. *Proc. Natl. Acad. Sci. USA*, 91: 11993-11997.
6. Haas, C., Lemere, C., Capell, A., Citron, M., and Selkoe, D. (1995) The Swedish mutation causes early onset Alzheimer's disease by B-secretase cleavage within the secretory pathway. *Nature Med.*, 1: 1291-1296.
7. Haas, C., Hung, A. Y., and Selkoe, S. J. (1991) Processing of Beta-Amyloid precursor protein in microglia and astrocytes favours an internal loclaization over constitutive secretion. *J. Neurosci.*, 11: 3783-3793.
8. Haas, C., Hung, A. Y., Selkoe, D. J., and Teplow, D. B. (1994) Mutations associated with a locus for familial Alzheimer's Disease result in alternative processing of amyloid B-protein precursor. *J. Biol. Chem.*, 269: 17741-17748.
9. Shoji, M., Golde, T., Ghiso, J., et al. (1992) Production of the Alzheimer amyloid B protein by normal proteolytic processing. *Science*, 258: 126-129.
10. Scott, M. R., Kohler, R., Foster, D., and Prusiner, S. B. (1992) Chimeric prion protein expression in cultured cells and transgenic mice. *Protein Sci.*, 1: 986-997.
11. Nee, L., Polinsky, R. J., Eldridge, R., Weingartner, H., Smallberg, S., and Ebert, M. (1983) A family with histologically confirmed Alzheimer Disease. *Arc. Neurol.*, 40: 203-208.
12. Foncin, J. -F., Salmon, D., Supino-Viterbo, V., Feldman, R. G., Macchi, G., Mariotti, P., Scopetta, C., Caruso, G., and Bruni, A. C. (1985) Alzheimer's Presenile dementia transmitted in an extended kindred. *Rev. Neurol. (Paris)*, 141: 194-202.
13. Frommelt, P., Schnabel, R., Kuhne, W., Nee, L. E., and Polinsky, R. J. (1991) Familial Alzheimer Disease: a large multigenerational German kindred. *Alzheimer Dis. Assoc. Disorders*, 5: 36-43.
14. Lippa, C. F., Saunders, A. M., Smith, T. W., et al. (1996) Familial and sporadic Alzheimer's disease: neuropathology cannot exclude a final common pathway. *Neurology*, 46: 406-412.
15. Lippa, C. F., Nee, L. E., Mori, H., and St George-Hyslop, P. (1998) Abeta42 deposition precedes other changes in PS1 Alzheimer's Disease. *Lancet*, 352: 1117-1118.
16. van Leuven, F. (2000) Single and multiple transgenic mice as models for Alzheimer's Disease. *Prog. Neurobiol.*, 61: 305-312.
17. Games, D., Adams, D., Alessandrini, A., et al. (1995) Alzheimer-type neuropathology in transgenic mice overexpressing V717F beta-amyloid precursor protein. *Nature*, 373: 523-527.
18. Hsiao, K., Chapman, P., Nilsen, S., Eckman, C., Horigoya, Y., Younkin, S., Yang, F. S., and Cole, G. (1996) Correlative memory deficits, Abeta elevation, and amyloid plaques in transgenic mice. *Science*, 274: 99-102.
19 Sturchler-Pierrat, C., Abramowski, D., Duke, M., Wiederhold, K. H., Mistl, C., Rothacher, S., Ledermann, B., Burki, K., Frey, P., Paganetti, P. A., Waridel, C., Calhoun, M. E., Jucker, M., Probst, A., Staufenbiel, M., and Sommer, B. (1997) *Proc. Natl. Acad. Sci USA* 94(24), 13287-92
20. Moechars, D., Dewachter, I., Lorent, K., et al. (1999) Early phenotypic changes in transgenic mice that overexpress different mutants of amyloid precursor protein. *J. Biol. Chem.*, 274: 6483-6492.
21. Citron, M., Eckman, C. B., Diehl, T. S., et al. (1998) Additive effects of PS1 and APP mutations on secretion of the 42-residue amyloid beta-protein. *Neurobiol. Dis.*, 5: 107-116.
22. Holcomb, L., Gordon, M. N., McGowan, E., et al. (1998) Accelerated Alzheimer-type phenotype in transgenic mice carrying both mutant amyloid precursor protein and pre-senilin 1 transgenes. *Nature Med.*, 4: 97-100.
23. Borchelt, D. R., Ratovitski, T., van Lare, J., Lee, M. K., Gonzales, V., Jenkins, N. A., Copeland, N. G., Price, D. L., and Sisodia, S. (1997) Accelarated amyloid deposition in brains of transgenic mice co-expressing mutant PS1 and Amyloid Precursor Protein. *Neuron*, 19: 939-945.
24. Palmiter, R. D., and Brinster, R. L. (1986) *Annu. Rev. Genet.* 20, 465-499.
25. Daniel C. Lu; Shahrooz Rabizadeh; Sreeganga Chandra; Rana F. Shayya; Lisa M. Ellerby; Xin Ye; Guy S. Salvesen; Edward H. Koo; Dale E. Bredesen. A second cytotoxic proteolytic peptide derived from amyloid beta-protein precursor. (2000) *Nature Medicine* 6, 397-404
26. Schenk, D., Barbour, R., Dunn, W., et al. (1999) Immunization with Abeta attenuates Alzheimer's Disease-like pathology in the PDAPP mouse. *Nature*, 400: 173-177.
27. Hsia A Y, Masliah E, McConlogue L, Yu G Q, Tatsuno G, Hu K, Kholodenko D, Malenka R C, Nicoll R A, Mucke L. (1999) Plaque-independent disruption of neural circuits in Alzheimer's disease mouse models. *Proc Natl Acad Sci USA.* 96, 3228-33.

28. Carlson G A, Borchelt D R, Dake A, Turner S, Danielson V, Coffin J D, Eckman C, Meiners J, Nilsen S P, Younkin S G, Hsiao K K (1997) Genetic modification of the phenotypes produced by amyloid precursor protein over-expression in transgenic mice. *Hum Mol Genet.* 6,1951-1959.
29. Hogan, B., Beddington, R., Costantini, F., and Lacy E. (1994) *Manipulating the Mouse Embryo.* Cold Spring Harbor Press, Cold Spring Harbour N.Y., USA.
30. Scott et al., (1989) *Cell* 59, 847-857
31. Morris, R. G. M. (1984) *J. Neuroscience Methods* 11, 47-60
32. Janus, C., D'Amelio, S., Amitay, O., Chishti, M. A., Strome, R., Frase, P. E., Carlson, G. A., Roder, J., St. Greoge-Hyslop, P. and Westway, D. (2000) *Neurobiology of Disease* in press
33. Feinberg, A. P., and Vogelstein, B. (1983) *Anal. Biochem.* 132, 6-13
34. Citron, M., Eckman, C. B., Diehl, T. S., Corcoran, C., Ostaszewski, B., L., Xia, W., Levesque, G., St. George Hyslop, P., Younkin, S. G., and Selkoe, D. J. (1998) *Neurobiol Dis* 5, 107-116).
35. Citron, M., Westaway, D., Xia, W., Carlson, G. A., Diehl, T., Levesque, G., Johnson-Wood, K., Lee, M., Seubert, P., Davis, A., Kholodenko, D., Motter, R., Sherrington, R., Perry, B., Yao, H., Strome, R., Lieberburg, I., Rommnes, J., Kim, S., Schenk, D., Fraser, P., St-George-Hyslop, P. and Selkoe, D., (1997) *Nature Medicine* 3, 67-72.
36. Schenk, D., Barbour, R., Dunn, W., Gordon, G., Grajeda, H., Guido, T., Hu, K., Huang, J., Johnson-Wood, K., Khan, K., Kholodenko, D., Lee, M., Liao, Z., Lieberburg, I., Motter, R., Mutter, L., Soriano, F., Shopp, G., Vasquez, N., Vandervert, C., Walker, S., Wogulis, M., Yednock, T., Games, D., and Seubert, P. (1999) *Nature* 400 (6740), 173-7.
37. Forss-Petter et al., (1990) *Neuron* 5 217.
38. Sasahara et al. (1991) *Cell* 64, 217.
39. McGowan et al., (1999), Neurobiol. of Disease, v. 6, pp. 231-244
40. Prusiner et al., (1990), *Cell* 63, 673-686.
41. Andra, K. Abramowski, D., Duke, M., Pobst, A., Wiederhold, K. H., Burki, K., Goedert, M., Sommer, B., and Staufenbiel, M. (1996). Expression of APP in transgenic mice: a comparison of neuron-specific promoters. *Neurobiol Aging* 17, 183-90.

TABLE 1

Properties of human APP-mutant transgenic mice exhibiting Aβ plaque deposits.

| APP line | APP mutation | Human APP isoform(s) | Age at onset for hippocampal Aβ amyloid plaques by immuno-staining | Age at onset for mature Aβ amyloid plaques (Congo Red staining) | Age at onset for deficits in hidden platform version of water-maze |
|---|---|---|---|---|---|
| PDAPP[17] | V717F | 695, 751, 770* | 8 months | ¶Not reported. | No deficits reported |
| Tg2576[18] | K670N, M671L | 695 | 9-11 months | ¶Not reported. | Impairment at 9-10 months in C57 × SJL strain background. |
| TgAPP23[19] | K670N, M671L | 751 | Rare deposits at 6 months | 6 months | No deficits reported |
| TgAPP22[19] | K670N, M671L plus V717I | 751 | 18 months | Sub-set of the plaques present at 18 months | No deficits reported |
| APP/Ld/2[20] | V717I | 695 | 13-18 months | ¶Not reported. | Impairment at 3-6 months in FVB/N × C57 strain background |
| TgCRND8 | K670N, M671L plus V717F | 695 | Multiple deposits at 3 months | A sub-set of plaques, appearing from 4-5 months onwards | Impairment at 2.8 months in C57 × C3H strain background |

*cDNA cassette includes introns to allow production of APP695, 751, and 770 spliced mRNAs.
¶Plaque deposits were reported to stain with Congo Red but ages were not stated. Staining with thioflavin-S was reported at 8 months in PDAPP mice and 354 days in Tg2576 mice.

TABLE 2

Properties of APP mutant x presenilin mutant crosses

| APP mutant parent | Presenilin mutant parent | Age at onset for hippocampal Aβ amyloid plaques by immuno-staining | Age at onset for mature Aβ amyloid plaques (Congo Red staining) | Age at onset for deficits in hidden platform version of water-maze |
|---|---|---|---|---|
| None | PS1 or PS2 mutant | None | None | None |
| TgCRND8 | None | 3 months | 4-5 months | 2.8 months‡ |
| TgCRND8 | PS1(L286V)1274 | 2 months | Not done | Not done |
| TgCRND8 | PS2(M239V)1379 | 2 months | Not done | 2.8 months‡ |
| TgCRND8 | PS1(M146L + L286 V) 6500 | 1 month | 1.5 months | Not done |
| Tg2576 | PS1(M146L) | 6 months, none at 3 months | 7 months | †Not reported |

†Deficits are reported for these mice in other paradigms (Y maze) and in "single-Tg" Tg2576 mice as per TABLE 1.
‡Testing mice at earlier ages is not routinely performed, as the mice need to reach a weight of 25 g and two-weeks of pre-training before testing in the water-maze paradigm.

We claim:

1. A C3H×C57 mouse or its progeny whose genome comprises a transgene comprising a nucleotide sequence operably linked to a Syrian hamster prion protein gene promoter and encoding a heterologous human amyloid precursor protein 695 (APP695) polypeptide wherein the lysine residue at position 670 is substituted by asparagine, the methionine residue at position 671 is substituted by leucine and the valine residue at position 717 is substituted by phenylalanine, wherein said promoter directs central nervous system or neuronal expression of said transgene and wherein said mouse displays abnormal Aβ deposition in its central nervous system.

2. The C3H×C57 mouse of claim 1 wherein the mouse is a (C3H×C57BL6)×C57 mouse.

3. The C3H×C57 mouse of claim 1 wherein the mouse displays abnormal Aβ deposition in its central nervous system by 3 months of age.

4. The C3H×C57 mouse of claim 1 wherein the mouse displays an appearance of Alzheimer's Disease-related pathology by 3 months of age.

5. A method of producing a C3H×C57 mouse that displays abnormal Aβ deposition in its central nervous system comprising:
   (a) introducing into a fertilized oocyte of said mouse a transgene comprising a nucleotide sequence operably linked to a Syrian hamster prion protein gene promoter and encoding a heterologous human amyloid precursor protein 695 (APP695) polypeptide wherein the lysine residue at position 670 is substituted by asparagine, the methionine residue at position 671 is substituted by leucine and the valine residue at position 717 is substituted by phenylalanine and wherein said Syrian hamster prion protein gene promoter directs central nervous system or neuronal expression of said transgene;
   (b) transplanting said fertilized oocyte into a pseudopregnant mouse;
   (c) allowing said fertilized oocyte to develop into a live born offspring; and
   (d) selecting an offspring where its genome comprises a transgene comprising a nucleotide sequence operably linked to a promoter and encoding a heterologous amyloid precursor protein 695 (APP695) polypeptide wherein the lysine residue at position 670 is substituted by asparagine, the methionine residue at position 671 is substituted by leucine and the valine residue at position 717 is substituted by phenylalanine and wherein the transgene is expressed.

6. A vector comprising a nucleotide sequence encoding a heterologous human amyloid precursor protein 695 (APP695) polypeptide wherein the lysine residue at position 670 is substituted by asparagine, the methionine residue at position 671 is substituted by leucine and the valine residue at position 717 is substituted by phenylalanine, and wherein said nucleotide sequence is operably linked to a Syrian hamster prion protein gene promoter.

7. A C3H×C57 mouse whose genome comprises a transgene comprising a nucleotide sequence operably linked to a Syrian hamster prion protein gene promoter and encoding a heterologous human amyloid precursor protein 695 (APP695) polypeptide wherein the lysine residue at position 670 is substituted by asparagine, the methionine residue at position 671 is substituted by leucine and the valine residue at position 717 is substituted by phenylalanine, wherein said promoter directs central nervous system or neuronal expression of said transgene, wherein said mouse displays abnormal Aβ deposition in its central nervous system, and wherein said mouse is made by the method of claim 5.

* * * * *